(12) United States Patent
Twomey et al.

(10) Patent No.: US 9,265,571 B2
(45) Date of Patent: Feb. 23, 2016

(54) SURGICAL FORCEPS

(71) Applicant: COVIDIEN LP, Mansfield, MA (US)

(72) Inventors: John R. Twomey, Superior, CO (US); James D. Allen, IV, Broomfield, CO (US); Kim V. Brandt, Loveland, CO (US); Keir Hart, Lafayette, CO (US); Daniel A. Joseph, Golden, CO (US); Jeffrey R. Unger, Longmont, CO (US)

(73) Assignee: Covidien LP, Mansfield, MA (US)

( * ) Notice: Subject to any disclaimer, the term of this patent is extended or adjusted under 35 U.S.C. 154(b) by 12 days.

(21) Appl. No.: 14/716,387

(22) Filed: May 19, 2015

(65) Prior Publication Data

US 2015/0245866 A1    Sep. 3, 2015

Related U.S. Application Data

(62) Division of application No. 13/461,410, filed on May 1, 2012, now Pat. No. 9,034,009.

(51) Int. Cl.
| | | |
|---|---|---|
| *A61B 17/28* | (2006.01) | |
| *A61B 18/14* | (2006.01) | |
| *A61B 17/285* | (2006.01) | |

(Continued)

(52) U.S. Cl.
CPC .......... *A61B 18/1445* (2013.01); *A61B 17/285* (2013.01); *A61B 17/2812* (2013.01); *A61B 17/2816* (2013.01); *A61B 18/1442* (2013.01); *A61B 2017/2947* (2013.01); *A61B 2018/0063* (2013.01); *A61B 2018/00077* (2013.01);

(Continued)

(58) Field of Classification Search
CPC .... A61B 17/28; A61B 17/2816; A61B 17/29; A61B 17/3201; A61B 18/1442; A61B 18/1445; A61B 2018/1455
See application file for complete search history.

(56) References Cited

U.S. PATENT DOCUMENTS

| | | |
|---|---|---|
| 2,305,156 A | 12/1942 | Grubel |
| 2,801,633 A | 8/1957 | Ehrlich |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

U.S. Appl. No. 13/249,024, John R. Twomey.

(Continued)

*Primary Examiner* — Julie A Szpira

(57) ABSTRACT

A forceps includes an end effector assembly having first and second jaw members. Each of the jaw members includes a proximal flange extending therefrom. Each of the proximal flanges defines a bifurcated configuration having first and second spaced-apart flange components. The first flange component of the first jaw member is configured to pivotably engage the second flange component of the second jaw member via a first protrusion-aperture coupling. The first flange component of the second jaw member is configured to pivotably engage the second flange component of the first jaw member via a second protrusion-aperture coupling different from the first protrusion-aperture coupling. One or both of the jaw members is pivotable relative to the other about the first and second protrusion-aperture couplings between a spaced-apart position and an approximated position for grasping tissue therebetween.

15 Claims, 7 Drawing Sheets

(51) Int. Cl.
*A61B 18/00* (2006.01)
*A61B 17/29* (2006.01)

(52) U.S. Cl.
CPC .............. *A61B2018/00083* (2013.01); *A61B 2018/00345* (2013.01); *A61B 2018/1455* (2013.01)

(56) References Cited

U.S. PATENT DOCUMENTS

| | | | |
|---|---|---|---|
| D249,549 S | 9/1978 | Pike | |
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,242,456 A | 9/1993 | Nash et al. | |
| 5,269,804 A | 12/1993 | Bales et al. | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| 5,383,471 A | 1/1995 | Funnell | |
| 5,389,104 A | 2/1995 | Hahnen et al. | |
| D358,887 S | 5/1995 | Feinberg | |
| 5,461,765 A | 10/1995 | Linden et al. | |
| D384,413 S | 9/1997 | Zlock et al. | |
| 5,707,392 A * | 1/1998 | Kortenbach | 606/207 |
| 5,776,156 A | 7/1998 | Shikhman | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| 6,117,158 A | 9/2000 | Measamer et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| 7,103,947 B2 | 9/2006 | Sartor et al. | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,491,207 B2 * | 2/2009 | Keyer et al. | 606/103 |
| 7,497,150 B1 | 3/2009 | Huang | |
| 7,544,200 B2 * | 6/2009 | Houser | 606/169 |
| 7,717,904 B2 * | 5/2010 | Suzuki et al. | 606/1 |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| 8,105,329 B2 | 1/2012 | Brumfield et al. | |
| RE43,317 E * | 4/2012 | Fraser et al. | 606/99 |
| D661,394 S | 6/2012 | Romero et al. | |
| 8,382,767 B2 * | 2/2013 | Wassinger et al. | 606/99 |
| 8,480,671 B2 * | 7/2013 | Mueller | 606/51 |
| 9,034,009 B2 | 5/2015 | Twomey et al. | |
| 2002/0058925 A1 | 5/2002 | Kaplan et al. | |
| 2008/0004629 A1 * | 1/2008 | Nichols et al. | 606/99 |
| 2008/0319442 A1 * | 12/2008 | Unger et al. | 606/48 |
| 2009/0043305 A1 * | 2/2009 | Brodbeck et al. | 606/52 |
| 2009/0088743 A1 | 4/2009 | Masuda | |
| 2009/0182327 A1 | 7/2009 | Unger | |
| 2010/0145334 A1 | 6/2010 | Olson et al. | |
| 2011/0009864 A1 | 1/2011 | Bucciaglia et al. | |
| 2012/0083786 A1 | 4/2012 | Artale et al. | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 20 2007 009317 U1 | 8/2007 |
| DE | 202007009165 U1 | 8/2007 |
| DE | 202007009318 U1 | 8/2007 |
| DE | 10031773 B4 | 11/2007 |
| DE | 202007016233 U1 | 1/2008 |
| DE | 102006059175 A1 | 6/2008 |
| DE | 19738457 B4 | 1/2009 |
| DE | 102004026179 B4 | 1/2009 |
| DE | 102008018406 B3 | 7/2009 |
| EP | 0584787 A1 | 3/1994 |
| EP | 1 159 926 A2 | 12/2001 |
| EP | 1810625 | 7/2007 |
| EP | 2347725 A1 | 7/2011 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |

(56) References Cited

FOREIGN PATENT DOCUMENTS

| | | | |
|---|---|---|---|
| JP | 11244298 | A | 9/1999 |
| JP | 2000-102545 | A | 4/2000 |
| JP | 2000342599 | A | 12/2000 |
| JP | 2000350732 | A | 12/2000 |
| JP | 2001008944 | A | 1/2001 |
| JP | 2001029356 | A | 2/2001 |
| JP | 2001-03400 | | 4/2001 |
| JP | 2001128990 | A | 5/2001 |
| JP | 2001-190564 | A | 7/2001 |
| JP | 2002-136525 | A | 5/2002 |
| JP | 2002-528166 | A | 9/2002 |
| JP | 2003-175052 | A | 6/2003 |
| JP | 2003245285 | A | 9/2003 |
| JP | 2004-517668 | A | 6/2004 |
| JP | 2004-528869 | A | 9/2004 |
| JP | 2005-253789 | A | 9/2005 |
| JP | 2006-015078 | A | 1/2006 |
| JP | 2006-501939 | A | 1/2006 |
| JP | 2006-095316 | A | 4/2006 |
| JP | 2011125195 | A | 6/2011 |
| SU | 401367 | A1 | 10/1973 |
| WO | 0036986 | A1 | 6/2000 |
| WO | 0059392 | A1 | 10/2000 |
| WO | 0115614 | A1 | 3/2001 |
| WO | 0154604 | A1 | 8/2001 |
| WO | 02/45589 | | 6/2002 |
| WO | 2006021269 | A1 | 3/2006 |
| WO | 2005110264 | A3 | 4/2006 |
| WO | 2008040483 | A1 | 4/2008 |
| WO | 2010/014825 | A1 | 2/2010 |

OTHER PUBLICATIONS

U.S. Appl. No. 13/251,380, Duane E. Kerr.
U.S. Appl. No. 13/277,373, Glenn A. Homer.
U.S. Appl. No. 13/277,926, David M. Garrison.
U.S. Appl. No. 13/277,962, David M. Garrison.
U.S. Appl. No. 13/293,754, Jeffrey M. Roy.
U.S. Appl. No. 13/306,523, David M. Garrison.
U.S. Appl. No. 13/306,553, Duane E. Kerr.
U.S. Appl. No. 13/308,104, John R. Twomey.
U.S. Appl. No. 13/312,172, Robert J. Behnke, II.
U.S. Appl. No. 13/324,863, William H. Nau, Jr.
U.S. Appl. No. 13/344,729, James D. Allen, IV.
U.S. Appl. No. 13/355,829, John R.Twomey.
U.S. Appl. No. 13/357,979, David M. Garrison.
U.S. Appl. No. 13/358,136, James D. Allen, IV.
U.S. Appl. No. 13/360,925, James H. Orszulak.
U.S. Appl. No. 13/400,290, Eric R. Larson.
U.S. Appl. No. 13/404,435, Kim V. Brandt.
U.S. Appl. No. 13/404,476, Kim V. Brandt.
U.S. Appl. No. 13/412,879, David M. Garrison.
U.S. Appl. No. 13/412,897, Joanna Ackley.
U.S. Appl. No. 13/421,373, John R. Twomey.
U.S. Appl. No. 13/430,325, William H. Nau, Jr.
U.S. Appl. No. 13/433,924, Keir Hart.
U.S. Appl. No. 13/448,577, David M. Garrison.
U.S. Appl. No. 13/460,455, Luke Waaler.
U.S. Appl. No. 13/461,335, James D. Allen, IV.
U.S. Appl. No. 13/461,378, James D. Allen, IV.
U.S. Appl. No. 13/461,397, James R. Unger.
U.S. Appl. No. 13/461,410, James R. Twomey.
U.S. Appl. No. 13/464,569, Duane E. Kerr.
U.S. Appl. No. 13/466,274, Stephen M. Kendrick.
U.S. Appl. No. 13/467,767, Duane E. Kerr.
U.S. Appl. No. 13/470,543, Sean T. Dycus.
U.S. Appl. No. 13/470,775, James D. Allen, IV.
U.S. Appl. No. 13/470,797, John J. Kappus.
U.S. Appl. No. 13/482,589, Eric R. Larson.
U.S. Appl. No. 13/483,733, Dennis W. Butcher.
U.S. Appl. No. 13/488,093, Kristin D. Johnson.
U.S. Appl. No. 13/491,853, Jessica E. Olson.
U.S. Appl. No. 13/537,517, David N. Heard.
U.S. Appl. No. 13/537,577, Tony Moua.
U.S. Appl. No. 13/550,322, John J. Kappus.
U.S. Appl. No. 13/571,055, Paul Guerra.
U.S. Appl. No. 13/571,821, Joseph D. Bucciaglia.
U.S. Appl. No. 13/584,194, Sean T. Dycus.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020528.9 dated Aug. 4, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 015215.8 dated Feb. 24, 2010.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175559.3 dated May 25, 2012.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019.9 dated Aug. 22, 2011.
Int'l Search Report EP 10 182022.3 dated Mar. 11, 2011.
Int'l Search Report EP 10 186527.7 dated Jun. 17, 2011.
Int'l Search Report Ep 10 189206.5 dated Mar. 17, 2011.
Int'l Search Report EP 10 191320.0 dated Feb. 15, 2011.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).

(56) References Cited

OTHER PUBLICATIONS

"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 11 006233.8 dated Feb. 2, 2012.
Int'l Search Report EP 11 007972.0 dated Dec. 28, 2011.
Int'l Search Report EP 11 151509.4 dated Jun. 6, 2011.
Int'l Search Report EP 11 152220.7 dated May 19, 2011.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05004431.2 dated Jun. 2, 2005.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.

(56) References Cited

OTHER PUBLICATIONS

Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 11 152360.1 dated Jun. 6, 2011.
Int'l Search Report EP 11 153503.5 dated Mar. 5, 2012.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report EP 11 180183 dated Nov. 30, 2011.
Int'l Search Report EP 11 183265.5 dated Nov. 28, 2011.
Int'l Search Report EP 11 183476.8 dated Jan. 18, 2012.
Int'l Search Report EP 11 185028.5 dated Jan. 2, 2012.
Int'l Search Report EP 11 189521.5 dated Feb. 20, 2012.
Int'l Search Report EP 11 190723.4 dated Mar. 16, 2012.
Int'l Search Report EP 12 155726.8 dated May 25, 2012.
Int'l Search Report EP 12 155728.4 dated Jul. 4, 2012.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/USO4/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report EP 10 185386.9 dated Jan. 10, 2011.
Int'l Search Report EP 10 185405.7 dated Jan. 5, 2011.
Int'l Search Report EP 11 168419.7 dated Oct. 20, 2011.
European Search Report from corresponding EP Application No. EP 13 16 6215 dated Apr. 29, 2014.
U.S. Appl. No. 08/926,869, James G. Chandler.
U.S. Appl. No. 09/177,950, Randel A. Frazier.
U.S. Appl. No. 09/387,883, Dale F. Schmaltz.
U.S. Appl. No. 09/591,328, Thomas P. Ryan.
U.S. Appl. No. 12/336,970, Paul R. Sremcich.
U.S. Appl. No. 13/050,182, Glenn A. Homer.
U.S. Appl. No. 13/072,945, Patrick L. Dumbauld.
U.S. Appl. No. 13/080,383, David M. Garrison.
U.S. Appl. No. 13/085,144, Keir Hart.
U.S. Appl. No. 13/091,331, Jeffrey R. Townsend.
U.S. Appl. No. 13/102,573, John R. Twomey.
U.S. Appl. No. 13/102,604, Paul E. Ourada.
U.S. Appl. No. 13/108,093, Boris Chernov.
U.S. Appl. No. 13/108,129, Boris Chernov.
U.S. Appl. No. 13/108,152, Boris Chernov.
U.S. Appl. No. 13/108,177, Boris Chernov.
U.S. Appl. No. 13/108,196, Boris Chernov.
U.S. Appl. No. 13/108,441, Boris Chernov.
U.S. Appl. No. 13/108,468, Boris Chernov.
U.S. Appl. No. 13/111,642, John R. Twomey.
U.S. Appl. No. 13/111,678, Nikolay Kharin.
U.S. Appl. No. 13/113,231, David M. Garrison.
U.S. Appl. No. 13/157,047, John R. Twomey.
U.S. Appl. No. 13/162,814, Barbara R. Tyrrell.
U.S. Appl. No. 13/166,477, Daniel A. Joseph.
U.S. Appl. No. 13/166,497, Daniel A. Joseph.
U.S. Appl. No. 13/179,919, Russell D. Hempstead.
U.S. Appl. No. 13/179,960, Boris Chernov.
U.S. Appl. No. 13/179,975, Grant T. Sims.
U.S. Appl. No. 13/180,018, Chase Collings.
U.S. Appl. No. 13/183,856, John R. Tvvomey.
U.S. Appl. No. 13/185,593, James D. Allen, IV.
U.S. Appl. No. 13/204,841, Edward J. Chojin.
U.S. Appl. No. 13/205,999, Jeffrey R. Unger.
U.S. Appl. No. 13/212,297, Allan J. Evans.
U.S. Appl. No. 13/212,308, Allan J. Evans.
U.S. Appl. No. 13/212,329, Allan J. Evans.
U.S. Appl. No. 13/212,343, Duane E. Kerr.
U.S. Appl. No. 13/223,521, John R. Twomey.
U.S. Appl. No. 13/227,220, James D. Allen, IV.
U.S. Appl. No. 13/228,742, Duane E. Kerr.
U.S. Appl. No. 13/231,643, Keir Hart.
U.S. Appl. No. 13/234,357, James D. Allen, IV.
U.S. Appl. No. 13/236,168, James D. Allen, IV.
U.S. Appl. No. 13/236,271, Monte S. Fry.
U.S. Appl. No. 13/243,628, William Ross Whitney.
U.S. Appl. No. 13/247,778, John R. Twomey.
U.S. Appl. No. 13/247,795, John R. Twomey.
U.S. Appl. No. 13/248,976, James D. Allen, IV.
U.S. Appl. No. 13/249,013, Jeffrey R. Unger.

* cited by examiner

SURGICAL FORCEPS

CROSS-REFERENCE TO RELATED APPLICATIONS

This application is a divisional application of U.S. patent application Ser. No. 13/461,410, filed on May 1, 2012, the entire contents of which are hereby incorporated herein by reference.

BACKGROUND

1. Technical Field

The present disclosure relates to surgical instruments and, more particularly, to surgical forceps for grasping, sealing and/or dividing tissue.

2. Background of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member that effectively severs the tissue after forming a tissue seal.

SUMMARY

In accordance with one aspect of the present disclosure, a forceps is provided. The forceps includes an end effector assembly having first and second jaw members. Each jaw member includes a proximal flange extending therefrom. Each of the proximal flanges defines a bifurcated configuration having first and second spaced-apart flange components. The first flange component of the first jaw member is configured to pivotably engage the second flange component of the second jaw member via a first protrusion-aperture coupling and the first flange component of the second jaw member is configured to pivotably engage the second flange component of the first jaw member via a second protrusion-aperture coupling different from the first protrusion-aperture coupling, at least one of the first and second jaw members pivotable relative to the other about the first and second protrusion-aperture couplings between a spaced-apart position and an approximated position for grasping tissue therebetween.

The proximal flanges may be disposed in an overlapping, offset configuration relative to one another.

In some aspects, the proximal flanges are formed via molding. Further, each of the proximal flanges may be monolithically formed with the respective jaw member thereof via molding. The proximal flanges may additionally or alternatively, be formed from an electrically-insulative material, e.g., plastic.

In any of the above aspects, the proximal flanges may each define a channel extending longitudinally therethrough. The channels of the proximal flanges cooperate with one another to permit reciprocation of a drive sleeve therethrough for moving the jaw members between the spaced-apart and approximated positions. The channels may also be configured to permit reciprocation of the knife therethrough for cutting tissue grasped between the jaw members.

Alternatively or additionally, each of the proximal flanges may include a protrusion extending outwardly from one of the flange components thereof and an aperture defined transversely through the other flange component thereof. The protrusion of each proximal flange is configured to engage the aperture of the other proximal flange for pivotably coupling the first and second jaw members to one another.

In some aspects, each of the jaw members includes an electrically-conductive tissue sealing plate disposed thereon. One or both of the sealing plates is adapted to connect to a source of energy for conducting energy through tissue grasped therebetween to seal tissue.

In accordance with another aspect of the present disclosure, a forceps including a shaft having an end effector disposed at a distal end thereof is provided. The shaft includes first and second opposed, transverse shaft apertures defined within an outer periphery thereof. The end effector assembly includes first and second jaw members pivotable relative to one another between a spaced-apart position and an approximated position for grasping tissue therebetween. Each jaw member includes a proximal flange extending therefrom. Each of the proximal flanges defines a bifurcated configuration having first and second spaced-apart flange components. The first flange component of the first jaw member includes a protrusion extending outwardly therefrom that is configured for pivotable engagement within a transverse aperture defined through the second flange component of the second jaw member. The first flange component of the second jaw member includes a protrusion extending outwardly therefrom that is configured for pivotable engagement within a transverse aperture defined through the second flange component of the first jaw member. A portion of each of the protrusions is configured to extend outwardly from the respective transverse aperture engaged therewith. The portion of each protrusion that extends outwardly from the apertures defined through the respective proximal flange engaged therewith is configured for pivotable engagement within one of the shaft apertures for engaging the first and second jaw members to the shaft. The forceps may further be configured to include any or all of the previous aspects discussed above.

BRIEF DESCRIPTION OF THE DRAWINGS

Various embodiments of the present disclosure are described herein with reference to the drawings wherein.

DETAILED DESCRIPTION

Figure 1:
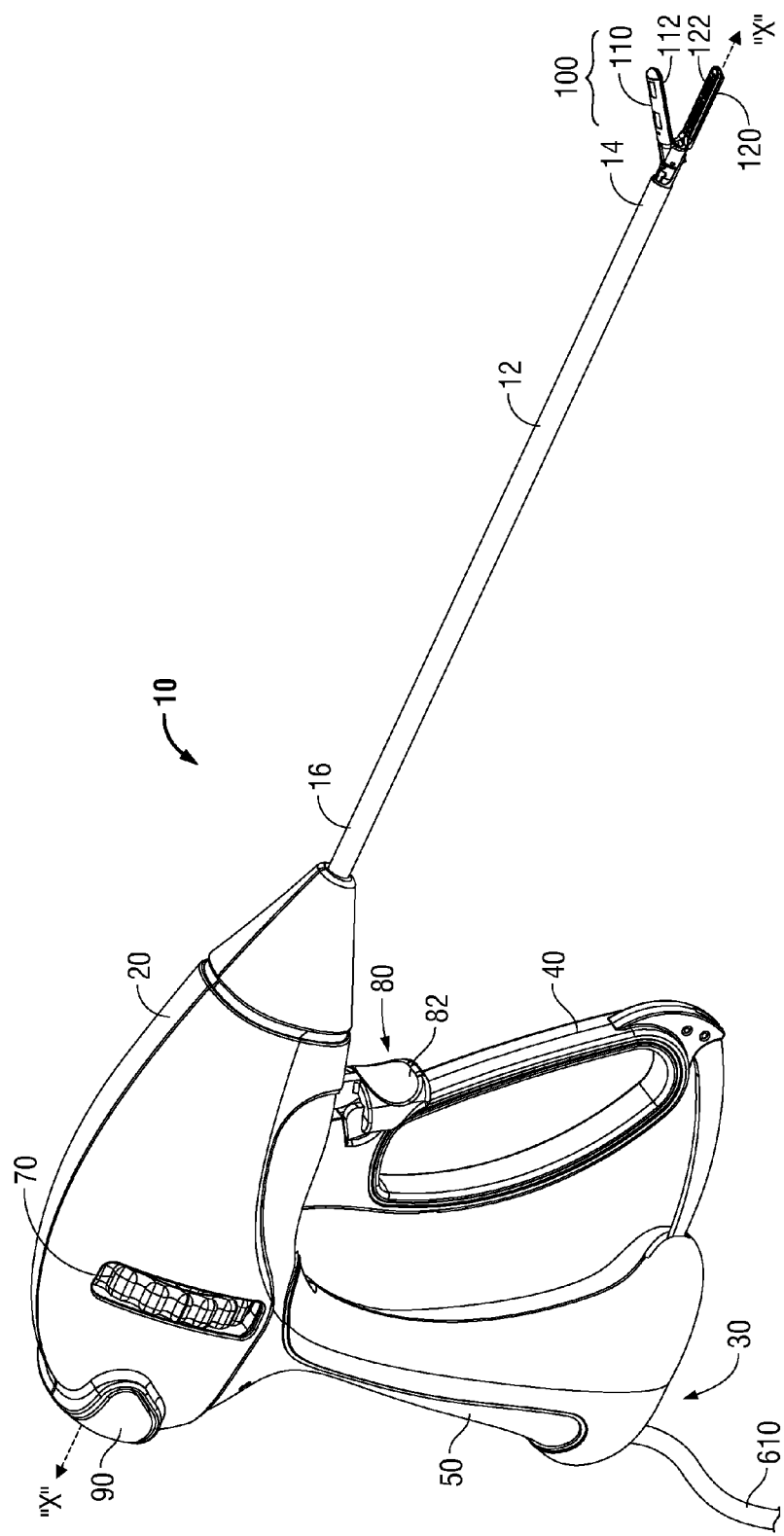
FIG. 1 is a front, perspective view of an endoscopic surgical forceps configured for use in accordance with the present disclosure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 2:
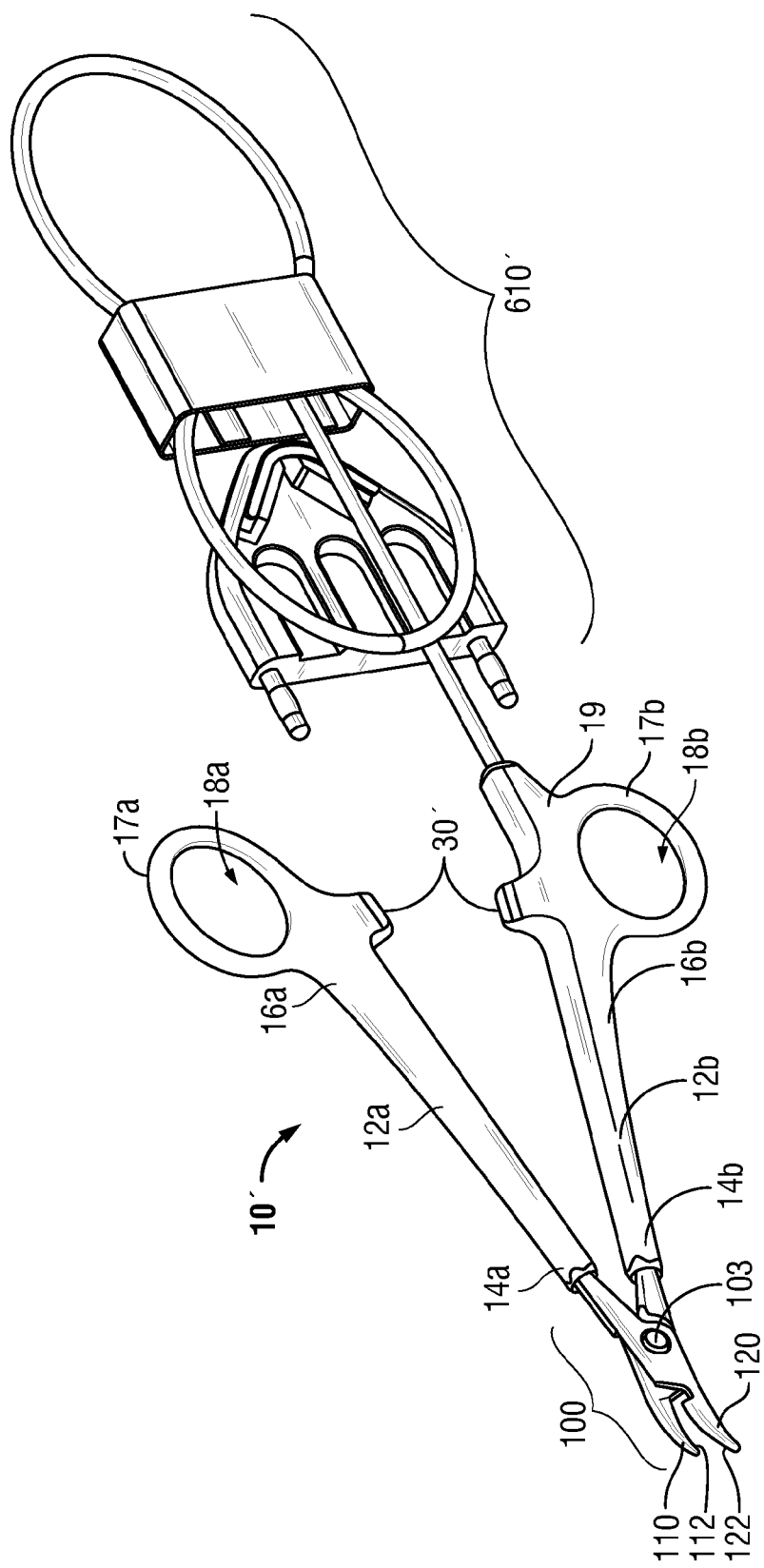
FIG. 2 is a front, perspective view of an open surgical forceps configured for use in accordance with the present disclosure.

Referring now to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic instrument, e.g., forceps 10, or an open instrument, e.g., forceps 10', may be utilized in accordance with the present disclosure. Obviously, different electrical and mechanical connections and considerations apply to each particular type of instrument, however, the novel aspects with respect to the end effector assembly and its operating characteristics remain generally consistent with respect to both the open and endoscopic configurations.

Turning now to FIG. 1, an endoscopic forceps 10 is provided defining a longitudinal axis "X-X" and including a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 610 that connects forceps 10 to a generator (not shown) or other suitable power source, although forceps 10 may alternatively be configured as a battery powered instrument. Cable 610 includes a wire (or wires) (not shown) extending therethrough that has sufficient length to extend through shaft 12 in order to provide electrical energy to at least one of the sealing plates 112, 122 of jaw members 110, 120, respectively, of end effector assembly 100, e.g., upon activation of activation switch 90.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about longitudinal axis "X-X" to rotate end effector 100 about longitudinal axis "X-X." Housing 20 houses the internal working components of forceps 10.

End effector assembly 100 is shown attached at a distal end 14 of shaft 12 and includes a pair of opposing jaw members 110 and 120. Each of the jaw members 110 and 120 includes an opposed electrically-conductive tissue sealing plate 112, 122, respectively. End effector assembly 100 is designed as a unilateral assembly, i.e., where jaw member 120 is fixed relative to shaft 12 and jaw member 110 is moveable relative to shaft 12 and fixed jaw member 120. However, end effector assembly 100 may alternatively be configured as a bilateral assembly, i.e., where both jaw member 110 and jaw member 120 are moveable relative to one another and to shaft 12. In some embodiments, a knife assembly 180 (FIGS. 8A-8C) is disposed within shaft 12 and a knife channel 115, 125 (FIGS. 8A-8C) is defined within one or both jaw members 110, 120 to permit reciprocation of a knife 184 (FIG. 8A-8C) therethrough, e.g., via activation of a trigger 82 of trigger assembly 80. The particular features of end effector assembly 100 will be described in greater detail hereinbelow.

Continuing with reference to FIG. 1, moveable handle 40 of handle assembly 30 is ultimately connected to a drive assembly (not shown) that, together, mechanically cooperate to impart movement of jaw members 110 and 120 between a spaced-apart position and an approximated position to grasp tissue disposed between sealing plates 112 and 122 of jaw members 110, 120, respectively. More specifically, the drive assembly (not shown) may include a drive sleeve 170 (FIG. 9) that is pivotably coupled to jaw member 110 (and/or jaw member 120) and is longitudinally translatable through shaft 12 and relative to end effector assembly 100 to pivot jaw member 110 relative to jaw member 120 between the spaced-apart and approximated positions for grasping tissue therebetween. As shown in FIG. 1, moveable handle 40 is initially spaced-apart from fixed handle 50 and, correspondingly, jaw members 110, 120 are in the spaced-apart position. Moveable handle 40 is actuatable from this initial position to a depressed position for translating drive sleeve 170 (FIG. 9) through shaft 12 and relative to end effector assembly 100 to move jaw members 110, 120 to the approximated position for grasping tissue therebetween (see FIGS. 8B-8C).

Referring now to FIG. 2, an open forceps 10' is shown including two elongated shafts 12a and 12b, each having a proximal end 16a and 16b, and a distal end 14a and 14b, respectively. Similar to forceps 10 (FIG. 1), forceps 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 that are pivotably coupled to one another. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another which, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet 30' may be included for selectively locking the jaw members 110 and 120 relative to one another at various positions during pivoting. Ratchet 30' may include graduations or other visual markings that enable the user to easily and quickly ascertain and control the amount of closure force desired between the jaw members 110 and 120.

With continued reference to FIG. 2, one of the shafts, e.g., shaft 12*b*, includes a proximal shaft connector 19 that is designed to connect the forceps 10' to a source of electrosurgical energy such as an electrosurgical generator (not shown). Proximal shaft connector 19 secures an electrosurgical cable 610' to forceps 10' such that the user may selectively apply electrosurgical energy to the electrically-conductive tissue sealing plates 112 and 122 of jaw members 110 and 120, respectively, as needed.

Forceps 10' may further include a knife assembly 180 (FIGS. 8A-8C) disposed within either of shafts 12*a*, 12*b* and a knife channel 115, 125 (FIG. 8A) defined within one or both of jaw members 110, 120, respectively, to permit reciprocation of a knife 184 (FIGS. 8A-8C) therethrough.

Figure 3:
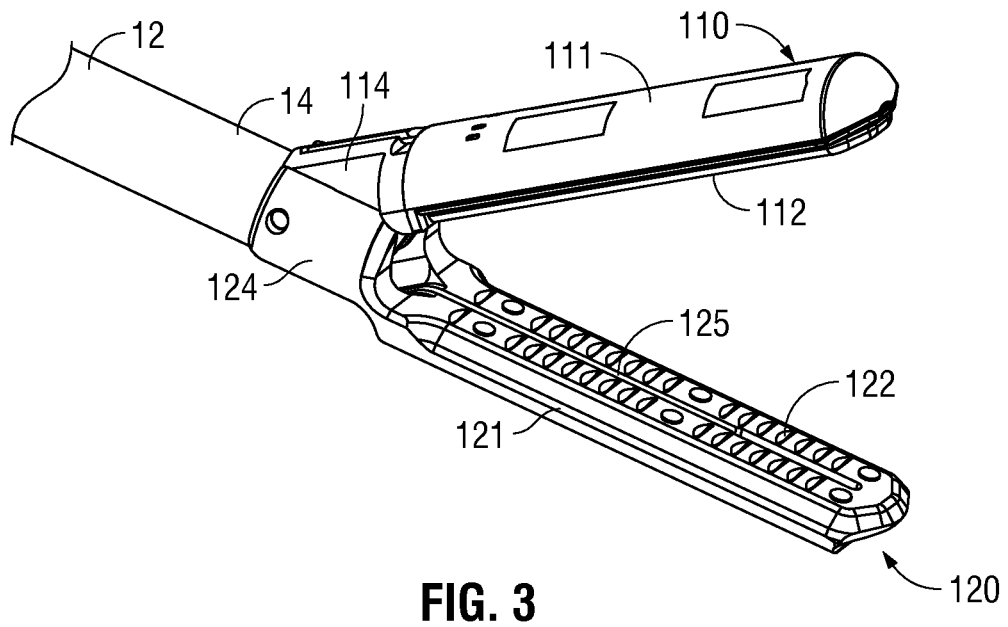
FIG. 3 is an enlarged, front, perspective view of an end effector assembly configured for use with the forceps of FIGS. 1 and 2.

Turning now to FIG. 3, end effector assembly 100, including jaw members 110 and 120 is configured for use with either forceps 10 or forceps 10', discussed above, or any other suitable surgical instrument capable of pivoting jaw members 110, 120 relative to one another between a spaced-apart position and an approximated position for grasping tissue therebetween. However, for purposes of simplicity and consistency, end effector assembly 100 will be described hereinbelow with reference to forceps 10 only.

Jaw members 110, 120, as shown in FIG. 3, each include an outer jaw housing 111, 121 and an electrically-conductive tissue sealing plate 112, 122 disposed atop respective jaw housings 111, 121. A proximal flange 114, 124 extends proximally from each of jaw housings 111, 121, respectively, for pivotably coupling jaw members 110, 120 to one another. Further, proximal flange 124 of jaw member 120 engages jaw member 120 to shaft 12. Alternatively, in embodiments where end effector assembly 100 is configured as a bilateral assembly, jaw member 120 is only coupled to jaw member 110 via proximal flange 124 and is not engaged to shaft 12 such that both jaw members 110, 120 may be pivoted relative to one another and to shaft 12 between the spaced-apart and approximated positions. Jaw housings 111, 121 of jaw members 110, 120, respectively, may be formed from stainless steel, or any other suitable material, e.g., electrically-insulative materials. Proximal flanges 114, 124 of jaw members 110, 120 define a bifurcated configuration, as will be described in greater detail below, and may be formed with jaw housings 111, 121, respectively, via molding or via any other suitable manufacturing process, e.g., machining, stamping, forging, or casting. In unilateral embodiments, proximal flange 124 of jaw member 120 may also be molded or otherwise engaged to shaft 12.

Electrically-conductive tissue sealing plates 112, 122 of jaw members 110, 120, respectively, each define an exposed tissue-sealing surface that opposes the tissue sealing surface defined by the sealing plate 112, 122 of the other jaw member 110, 120. Tissue sealing plates 112, 122 of jaw members 110, 120, respectively, are adapted to connect to a source of energy (not explicitly shown), thus functioning as electrodes for conducting energy therebetween and through tissue to treat tissue.

Proximal flanges 114, 124 of jaw members 110, 120, respectively, are formed from electrically-insulative materials, e.g., plastic, to inhibit shorting of tissue sealing plates 112, 122 during tissue treatment. Alternatively, proximal flanges 114, 124 may be formed from stainless steel, or other conductive materials so long as flanges 114, 124 are isolated from tissue sealing plates 112, 122. More specifically, since flanges 114, 124 of jaw members 110, 120, respectively, are pivotably coupled to one another, e.g., to permit movement of jaw members 110, 120 relative to one another between the spaced-apart and approximated positions, forming flanges 114, 124 from electrically-insulative materials (or isolating flanges 114, 124) inhibits direct electrical contact between tissue sealing plates 112, 122 of jaw members 110, 120, respectively, thus inhibiting shorting and/or damage to surrounding tissue. Forming proximal flanges 114, 124 from plastic, for example, also allows for relatively inexpensive manufacture, as the molding process is a relatively inexpensive process for forming proximal flanges 114, 124 with complex features to facilitate the pivotable coupling therebetween. The specific configurations and features of proximal flanges 114, 124 of jaw members 110, 120, respectively, will be described in greater detail below. Shaft 12 may likewise be formed from a plastic (or other suitable material) and, in unilateral embodiments, as mentioned above, may be molded with proximal flange 124 of jaw member 120 to form a single component. Forming shaft 12 from an electrically-insulative material, e.g., plastic, (or insolating shaft 12 from tissue sealing plates 112, 122, where shaft 12 is formed from a conductive material) also helps to maintain the electrical isolation between tissue sealing plates 112, 122 of jaw members 110, 120, respectively, thus inhibiting shorting of tissue sealing plates 112, 122 and/or damage to surrounding tissue (see FIG. 7D), although other configurations are also contemplated.

Figure 4:
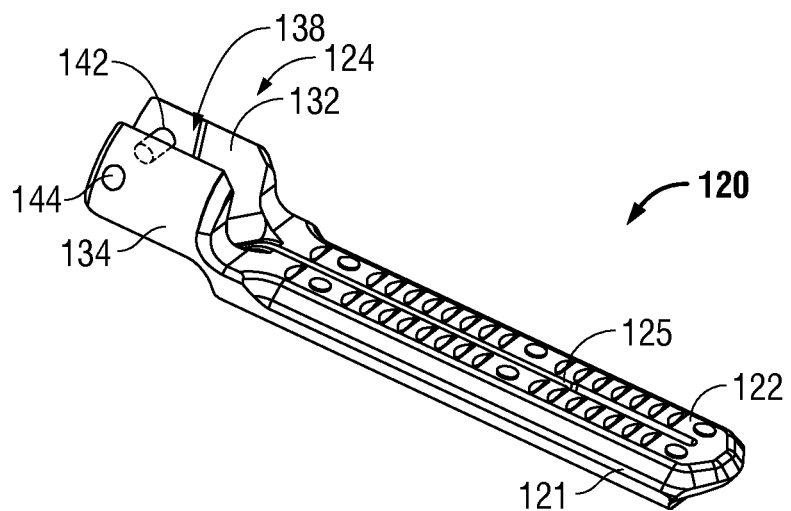
FIG. 4 is an enlarged, front, perspective view of one of the jaw members of the end effector assembly of FIG. 3.
Figure 5:
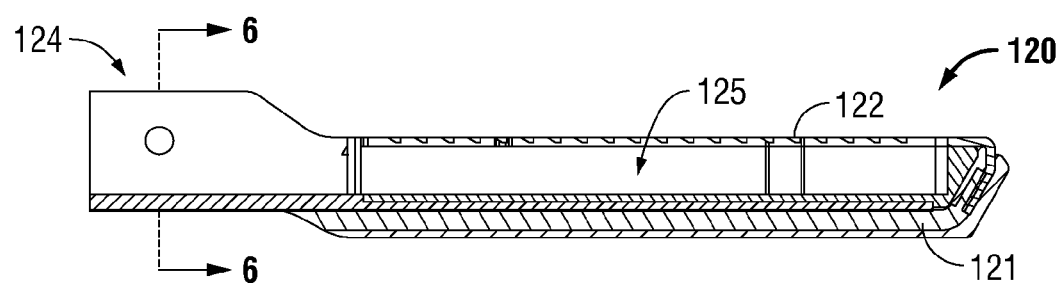
FIG. 5 is a longitudinal, cross-sectional view of the jaw member of FIG. 4.
Figure 6:
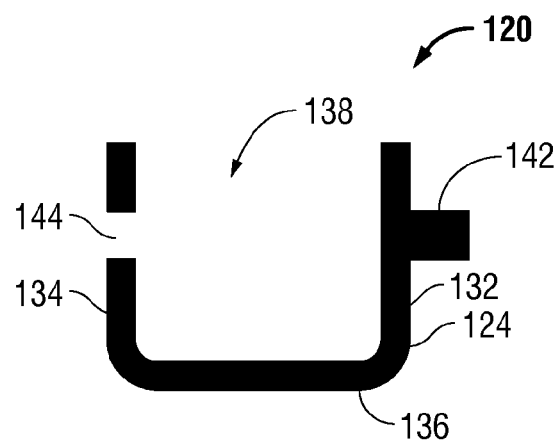
FIG. 6 is a transverse, cross-sectional view of the jaw member of FIG. 4 taken across section line 6-6 of FIG. 5.

With reference to FIGS. 4-6, jaw member 120 includes, as mentioned above, outer jaw housing 121, electrically-conductive tissue sealing plate 122 disposed atop outer jaw housing 121, and proximal flange 124 extending proximally from outer jaw housing 121 and configured to pivotably couple to proximal flange 114 of jaw member 110 (see FIG. 3). More specifically, proximal flange 124 defines a generally U-shaped, bifurcated configuration including first and second spaced-apart flange components 132, 134 that are interconnected by a base 136. Flange components 132, 134 define a channel 138 extending longitudinally therebetween that, as will be described below, is configured to receive at least a portion of proximal flange 114 of jaw member 110 (see FIG. 3) for pivotably coupling jaw members 110, 120 (FIG. 3) to one another and to permit longitudinal translation of drive sleeve 170 (FIG. 9) and knife 184 (FIGS. 8A-9) therethrough for moving jaw members 110, 120 (FIG. 3) between the spaced-apart and approximated positions and for translating knife 184 (FIGS. 8A-9) between a retracted and an extended position for cutting tissue grasped between jaw members 110, 120 (FIG. 3), respectively.

Continuing with reference to FIGS. 4-6, flange component 132 of proximal flange 124 of jaw member 120 includes a generally cylindrically-shaped protrusion 142 extending outwardly therefrom. Protrusion 142 may be monolithically formed with proximal flange 124 during the molding process, or any other suitable manufacturing process used, e.g., machining, stamping, forging, or casting. Flange component 134, on the other hand, defines an aperture 144 extending transversely therethrough that is substantially aligned with protrusion 142. Aperture 144 may be formed within flange component 134 during the manufacturing process, e.g., the molding process. Forming protrusion 142 on flange component 132 and defining aperture 144 through flange component 134 via the molding process is advantageous in that precise alignment of protrusion 142 and aperture 144 relative to one another can be achieved relatively easily.

Proximal flange 114 of jaw member 110, as shown in FIGS. 3 and 7A-7C, similarly defines a bifurcated, generally U-shaped configuration having first and second spaced-apart flange components 152, 154 interconnected by a base 156 and defining a channel 158 extending longitudinally therebetween. Similarly as with proximal flange 124 of jaw member 120, flange component 152 of proximal flange 114 includes a protrusion 162 extending outwardly therefrom, while flange component 154 defines an aperture 164 extending transversely therethrough. The specific features described herein with respect to proximal flange 124 of jaw member 120 apply similarly to proximal flange 114 of jaw member 110.

Figure 7A:
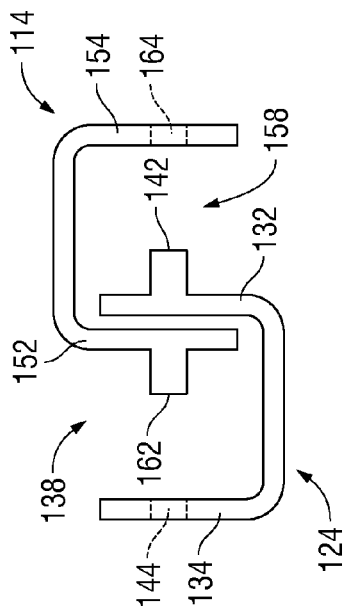
FIG. 7A is a transverse, cross-sectional view of the jaw members of end effector assembly of FIG. 3, wherein the jaw members are disengaged from one another.

With reference now to FIGS. 7A-7D, in conjunction with FIG. 3, the pivotable coupling of jaw members 110, 120 to one another and to shaft 12 is described. Initially, as shown in FIG. 7A, jaw member 110 is inverted relative to jaw member 120 such that tissue sealing plates 112, 122 of jaw members 110, 120, respectively, oppose one another. In this position, the U-shaped proximal flanges 114, 124 of jaw members 110, 120 oppose one another such that proximal flanges 114, 124 may be at least partially inserted into the channel 138, 158 defined within the opposed proximal flange 114, 124, respectively.

Figure 7B:
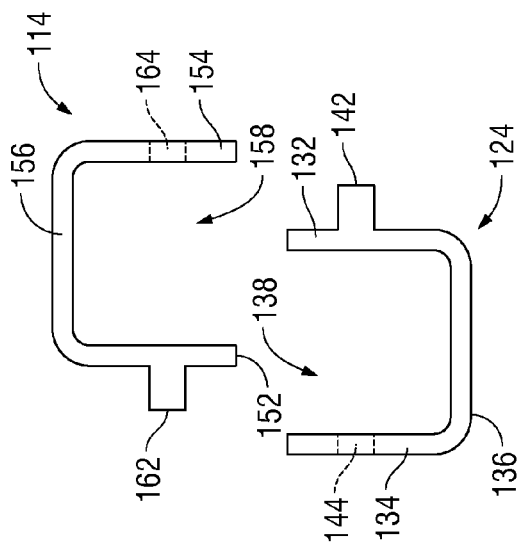
FIG. 7B is a transverse, cross-sectional view of the jaw members of end effector assembly of FIG. 3, wherein the jaw members are in position to be engaged with one another.

Continuing with reference to FIGS. 3 and 7A-7D, and in particular to FIG. 7B, with jaw member 110 inverted relative to jaw member 120, proximal flanges 114, 124 are approximated relative to one another such that flange component 132 is disposed within channel 158 of proximal flange 114 of jaw member 110 and such that flange component 152 is disposed within channel 138 of proximal flange 124 of jaw member 120. In other words, in this position, proximal flanges 114, 124 are disposed in an overlapping, but offset configuration wherein protrusion 142 of flange component 132 is positioned adjacent aperture 164 of flange component 154 and wherein protrusion 162 of flange component 152 is positioned adjacent aperture 144 of flange component 134.

Figure 7C:
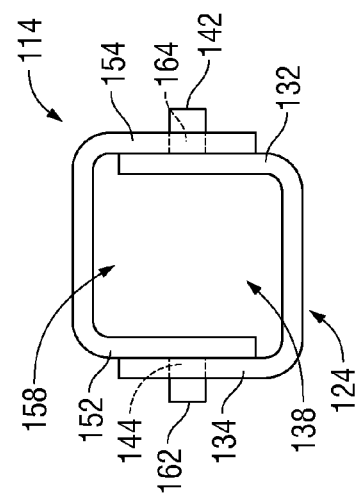
FIG. 7C is a transverse, cross-sectional view of the jaw members of end effector assembly of FIG. 3, wherein the jaw members are engaged with one another.

In order to pivotably engage proximal flange 114 of jaw member 110 and proximal flange 124 of jaw member 120 to one another, with proximal flanges 114, 124 disposed in the offset, overlapping configuration shown in FIG. 7B, proximal flanges 114, 124 are urged toward one another such that protrusion 142 of flange component 132 is engaged within aperture 164 of flange component 154 and such that protrusion 162 of flange component 152 is engaged within aperture 144 of flange component 134, as shown in FIG. 7C. In this position, flange components 132, 154 are pivotably coupled to and are substantially abutting one another and, similarly, flange components 134, 152 are pivotably coupled to and are substantially abutting one another. As such, jaw members 110, 120 may be simultaneously pivoted about these two protrusion-aperture couplings (e.g., the engagement between protrusion 142 and aperture 164 and the engagement between protrusion 162 and aperture 144) relative to one another to move jaw members 110, 120 between the spaced-apart and approximated positions for grasping tissue therebetween.

Figure 7D:
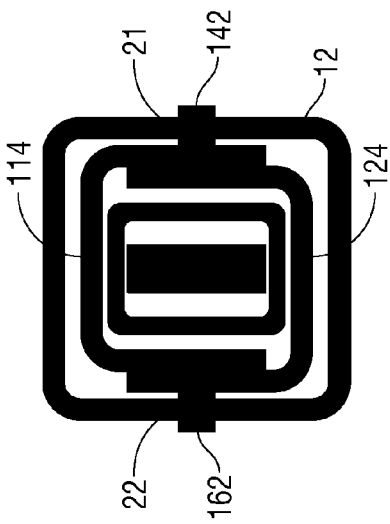
FIG. 7D is a transverse, cross-sectional view of the jaw members of end effector assembly of FIG. 3, wherein the jaw members are engaged to a shaft of the forceps of FIG. 1.

As shown in FIG. 7D, in order to engage end effector assembly 100 to shaft 12, e.g., in bilateral embodiments, or to provide additional stability and support to end effector assembly 100, protrusions 142, 162 are engaged within opposed transverse apertures 21, 22, respectively, defined through the outer periphery of shaft 12 towards distal end 14 (FIG. 3) thereof. More specifically, as shown in FIG. 7C, when protrusion 142 of flange component 132 is engaged within aperture 164 of flange component 154, protrusion 142 extends outwardly at least partially therefrom. Similarly, when protrusion 162 of flange component 152 is engaged within aperture 144 of flange component 134, protrusion 162 extend outwardly at least partially therefrom. As such, these outwardly-extending portions of protrusions 142, 162 may be pivotably engaged within transverse apertures 21, 22, respectively, defined within shaft 12 for engaging end effector assembly 100 to shaft 12 at distal end 14 (FIG. 3) thereof and for stabilizing and supporting the protrusion-aperture couplings between proximal flanges 114, 124 of jaw members 110, 120, respectively.

The pivotable coupling of bifurcated proximal flanges 114, 124 of jaw members 110, 120, e.g., via engagement between protrusions 142, 162 and apertures 164, 144, respectively, is advantageous in that channels 138, 158 defined within proximal flanges 124, 114, respectively, are substantially uninterrupted. For example, due to this configuration, knife 184 (FIGS. 8A-9) need not be configured to pass over/under a pivot pin or define a slot therein for receiving the pivot pin therethrough since, instead of a pivot pin extending transversely through channels 138, 158 of proximal flanges 124, 114, respectively, proximal flanges 114, 124 are pivotably coupled to one another via a protrusion-aperture coupling on either side of channels 138, 158.

Although proximal flanges 114, 124 are shown each including a protrusion 162, 142 and an aperture 164, 144, respectively, it is also envisioned that one of proximal flanges 114, 124 may include both protrusions, while the other proximal flange 114, 124 includes both apertures. Protrusions 162, 142 may also be configured to extend inwardly into channels 158, 138 of proximal flanges 114, 124, respectively, as opposed to outwardly (as shown). Further, one of the flange components 114, 124 may be disposed completely within the channel 138, 158 of the other flange component 114, 124, rather than defining the offset, overlapping configuration shown in FIG. 7C.

Figure 8A:
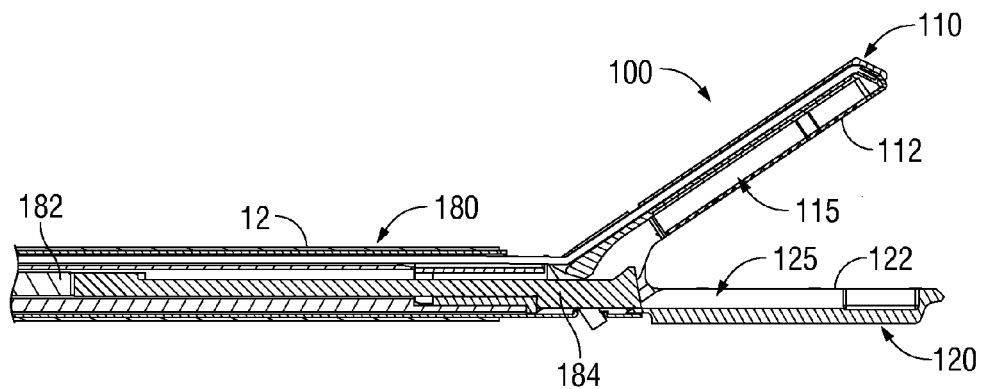
FIG. 8A is a longitudinal, cross-sectional view of the end effector assembly of FIG. 3 with the jaw members disposed in a spaced-apart position.
Figure 8B:
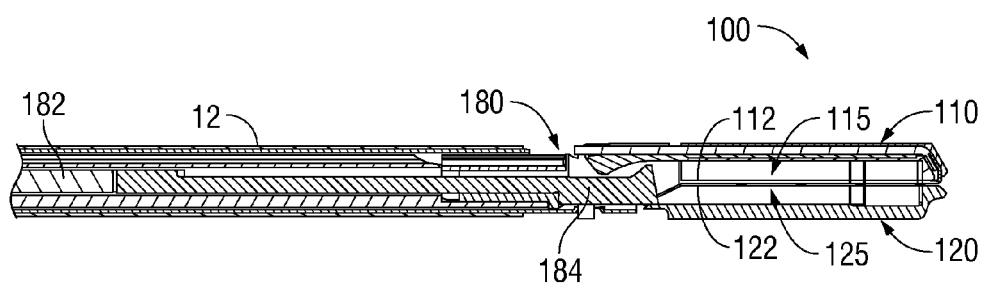
FIG. 8B is a longitudinal, cross-sectional view of the end effector assembly of FIG. 3 with the jaw members disposed in an approximated position and with a knife blade disposed in a retracted position.
Figure 8C:
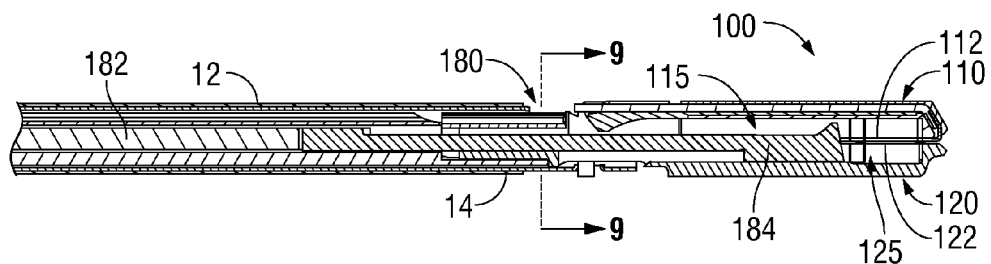
FIG. 8C is a longitudinal, cross-sectional view of the end effector assembly of FIG. 3 with the jaw members disposed in an approximated position and with the knife blade disposed in an extended position.
Figure 9:
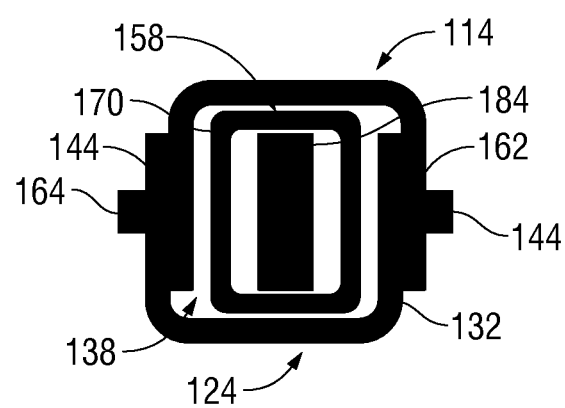
FIG. 9 is a transverse, cross-sectional view of the end effector assembly of FIG. 3 taken across section line 9-9 of FIG. 8C.

Referring now to FIGS. 8A-9, as mentioned above, in some embodiments, end effector assembly 100 includes a knife assembly 180 for cutting tissue disposed between jaw members 110, 120. Knife assembly 180 includes a knife bar 182 that is selectively translatable through shaft 12, e.g., upon activation of actuation trigger 82 (FIG. 1) of trigger assembly 80 (FIG. 1). Knife bar 182 includes a knife 184 coupled thereto and extending distally therefrom. As will be described below, knife bar 182 is selectively translatable to translate knife 184 between a retracted position, wherein knife 184 is disposed within shaft 12, and an extended position, wherein knife 184 extends through knife channels 115, 125 of jaw members 110, 120, respectively, to cut tissue grasped therebetween.

With continued reference to FIGS. 8A-9, the use and operation of end effector assembly 100 is described. Initially, as shown in FIG. 8A, with jaw members 110, 120 disposed in the spaced-apart position, end effector assembly 100 is maneuvered into position such that tissue to be grasped, treated, e.g., sealed, and/or cut, is disposed between jaw members 110, 120. Next, moveable handle 40 (FIG. 1) is pulled proximally relative to fixed handle 50 (FIG. 1) such that jaw member 110 is pivoted relative to jaw member 120 about the pair of protrusion-aperture couplings between proximal flanges 114, 124 of jaw members 110, 140, respectively, from the spaced-apart position to the approximated position to grasp tissue therebetween, as shown in FIG. 8B. More specifically, upon actuation of moveable handle 40 (FIG. 1), drive sleeve 170 is translated through shaft 12 and channels 138, 158 of proximal flanges 124, 114, of jaw members 120, 110, respectively, such that jaw member 110 is pivoted relative to jaw member 120 from the spaced-apart position to the approximated position. In this approximated position, electrosurgical energy may be supplied, e.g., via activation of switch 90 (FIG. 1), to tissue-sealing plate 112 of jaw member 110 and/or tissue-sealing plate 122 of jaw member 120 and conducted through tissue to treat tissue, e.g., to effect a tissue seal.

As shown in FIG. 8C, once tissue sealing is complete (or to cut untreated tissue, where tissue sealing is not desired), knife 184 may then be advanced through channels 158, 138 of proximal flanges 114, 124, respectively, from the retracted position (FIG. 8B) to the extended position (FIG. 8C), e.g., via activation of trigger 82 of trigger assembly 80 (FIG. 1), wherein knife 184 extends through knife channels 115, 125 of jaw members 110, 120, respectively, to cut tissue grasped between jaw members 110, 120. Thereafter, jaw members 110, 120 may be returned to the spaced-apart position (FIG. 8A) and removed from the surgical site, or the above-described process may be repeated to grasp, treat and/or divide additional tissue structures.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
    an end effector assembly, including:
        first and second jaw members, each of the jaw members including a distal body portion and a proximal flange, each proximal flange defining a bifurcated configuration having first and second spaced-apart flange components, the proximal flanges of the first and second jaw members disposed in an offset configuration wherein the first or second flange component of the first jaw member is disposed between the first and second flange components of the second jaw member and wherein the first or second flange component of the second jaw member is disposed between the first and second flange components of the second jaw member, the first flange component of the first jaw member coupled to the second flange component of the second jaw member via a first pivotable engagement and the first flange component of the second jaw member coupled to the second flange component of the first jaw member via a second, different pivotable engagement, wherein the first pivotable engagement is a first protrusion-aperture engagement and wherein the second pivotable engagement is a second, different protrusion-aperture engagement, the proximal flanges of the first and second jaw members cooperating to define a channel extending longitudinally therethrough between the first and second pivotable engagements; and
    a knife configured for reciprocation through the channel between the first and second pivotable engagements to permit reciprocation of the knife at least partially between the distal body portions of the first and second jaw members.

2. The forceps according to claim 1, wherein each of the proximal flanges is monolithically formed with the respective distal body portion of the jaw member thereof.

3. The forceps according to claim 1, wherein the proximal flanges are formed from an electrically-insulative material.

4. The forceps according to claim 1, wherein the channel is further configured to permit reciprocation of a drive sleeve therethrough for moving at least one of the first and second jaw members relative to the other between spaced-apart and approximated positions.

5. The forceps according to claim 4, wherein the knife is slidably disposed within the drive sleeve.

6. The forceps according to claim 1, wherein each of the proximal flanges includes a protrusion extending outwardly from the first or second flange component thereof and an aperture defined transversely through the other of the first or second flange component thereof, the protrusion of each proximal flange configured to engage the aperture of the other proximal flange to pivotably couple the first and second jaw members to one another via the first and second protrusion-aperture engagements.

7. The forceps according to claim 1, wherein each of the jaw members includes an electrically-conductive tissue sealing plate disposed on the distal body portion thereof, at least one of the sealing plates adapted to connect to a source of energy for conducting energy therebetween.

8. A forceps, comprising:
    a shaft defining a longitudinally-extending lumen therethrough and first and second opposed, transverse shaft apertures defined within an outer periphery thereof towards a distal end of the shaft;
    an end effector assembly disposed at a distal end of the shaft, the end effector assembly including first and second jaw members, each of the jaw members including a distal body portion and a proximal flange, each proximal flange defining a bifurcated configuration having first and second spaced-apart flange components, the first flange component of the first jaw member, the second flange component of the second jaw member, and the first transverse shaft aperture of the shaft coupled to one another via a first pivotable engagement, the first flange component of the second jaw member, the second flange component of the first jaw member, and the second transverse shaft aperture of the shaft coupled to one another via a second, different pivotable engagement, wherein the first pivotable engagement is a first protrusion-aperture engagement and wherein the second pivotable engagement is a second, different protrusion-aperture engagement, the proximal flanges of the first and second haw members cooperating to define a channel extending longitudinally therethrough between the first and second pivotable engagements, the channel disposed in communication with the lumen of the shaft; and
    a knife disposed within the lumen of the shaft and configured for reciprocation through the channel between the first and second pivotable engagements to permit reciprocation of the knife at least partially between the distal body portions of the first and second jaw members.

9. The forceps according to claim 8, wherein the proximal flanges of the first and second jaw members are disposed in an offset configuration wherein the first or second flange component of the first jaw member is disposed between the first and second flange components of the second jaw member and wherein the first or second flange component of the second jaw member is disposed between the first and second flange components of the second jaw member.

10. The forceps according to claim 8, wherein each of the proximal flanges is monolithically formed with the respective distal body portion of the jaw member thereof.

11. The forceps according to claim 8, wherein the proximal flanges are formed from an electrically-insulative material.

12. The forceps according to claim 8, wherein the channel is further configured to permit reciprocation of a drive sleeve therethrough for moving at least one of the first and second jaw members relative to the other between spaced-apart and approximated positions.

13. The forceps according to claim 12, wherein the knife is slidably disposed within the drive sleeve.

14. The forceps according to claim 8, wherein each of the proximal flanges includes a protrusion extending outwardly from one of the flange components thereof and an aperture defined transversely through the other flange component thereof, the protrusion of each proximal flange configured to engage the aperture of the other proximal flange and one of the transverse shaft apertures of the shaft to pivotably couple the first and second jaw members to one another and the shaft via the first and second protrusion-aperture engagements.

15. The forceps according to claim 8, wherein each of the jaw members includes an electrically-conductive tissue sealing plate disposed on the distal body portion thereof, at least one of the sealing plates adapted to connect to a source of energy for conducting energy therebetween.

\* \* \* \* \*